United States Patent [19]

Brunnschweiler et al.

[11] Patent Number: 4,733,080
[45] Date of Patent: Mar. 22, 1988

[54] TEXTILE STRUCTURE MEASURMENT

[75] Inventors: David Brunnschweiler, Balderstone; Peter G. Johnson; Neil R. Henderson, both of Blackburn, all of England

[73] Assignee: Haigh-Chadwick Limited, West Yorkshire, England

[21] Appl. No.: 835,250

[22] Filed: Mar. 3, 1986

[30] Foreign Application Priority Data

Mar. 9, 1985 [GB] United Kingdom ............... 8506149

[51] Int. Cl.⁴ ............................................. G01N 21/59
[52] U.S. Cl. ................................ 250/341; 250/359.1; 250/349
[58] Field of Search ................ 250/341, 559, 358.1, 250/359.1, 339, 349; 356/381, 429

[56] References Cited

U.S. PATENT DOCUMENTS

| | | | |
|---|---|---|---|
| 2,900,512 | 8/1959 | Jolly | 250/341 |
| 3,661,462 | 5/1972 | Natens | 250/339 |
| 3,806,730 | 4/1974 | Tirkkonen et al. | 250/341 |
| 3,906,232 | 9/1975 | Meihofer | 250/341 |
| 4,052,615 | 10/1977 | Cho | 250/341 |
| 4,363,968 | 12/1982 | McGowan et al. | 250/341 |

FOREIGN PATENT DOCUMENTS

| | | |
|---|---|---|
| 818271 | 10/1951 | Fed. Rep. of Germany . |
| 1905994 | 9/1970 | Fed. Rep. of Germany . |
| 2317992 | 10/1973 | Fed. Rep. of Germany . |
| 2449584 | 4/1975 | Fed. Rep. of Germany . |
| 3323214 | 10/1984 | Fed. Rep. of Germany ...... 356/381 |
| 3233507 | 4/4983 | Fed. Rep. of Germany . |
| 1308953 | 3/1973 | United Kingdom . |
| 1352700 | 5/1974 | United Kingdom . |
| 1364439 | 8/1974 | United Kingdom . |
| 1589152 | 5/1981 | United Kingdom . |
| 2095828 | 10/1982 | United Kingdom . |

Primary Examiner—Carolyn E. Fields
Attorney, Agent, or Firm—Oblon, Fisher, Spivak, McClelland, & Maier

[57] ABSTRACT

Thick textile structures such as cross folded card webs, where most of the transmitted light is light that has passed through the fibres of the textile structure, can be measured by measuring transmission through the said structure from an infra-red source, such for example, as a tungsten filament lamp run at a dull glow.

9 Claims, 4 Drawing Figures

TEXTILE STRUCTURE MEASURMENT

BACKGROUND TO THE INVENTION

This invention relates to measuring across textile structures.

It is known to measure properties of textile structures, and particularly fibre webs intended for making yarn or for non-woven textiles, by measuring the obscuring effect of the structure on a light source. A light source is disposed on one side of the web or other structure and a light sensor on the other side. This works quite well and is reasonably linear for light webs where the web fibres obscure up to about 75% of the direct illumination to the light sensor. At higher densities, however, most of the transmitted light is light that has passed through the fibres of the textile structure. The amount of light thus transmitted depends to a considerable extent upon the composition of the fibres, the filament cross-section, the nature and quantity of dye in or on the fibres, whether the fibres have optical brightening agents and like factors.

The present invention provides a method and apparatus for measuring across thick textile structures which is not subject to all the aforesaid disadvantages.

SUMMARY OF THE INVENTION

The invention comprises a method for measuring across a thick textile structure comprising measuring transmission through the said structure from an infra-red source The infra-red source may comprise a wide-band source, which may comprise a tungsten filament lamp, for example, run at a dull glow. By using a wide-band source, the possibility is avoided or reduced of absorption lines in the transmission spectrum affecting the measurement at certain wavelengths. On the other hand, provided that the infra-red properties of the particular fibre or fibres being measured are known, specific measurement frequencies may be selected by the use of appropriate filters. Of course, when reference is made to a tungsten lamp, which tends generally to be a small, if not exactly a point source, it is intended that where wide webs are concerned, several tungsten lamps will be used spaced apart at intervals to provide a spread of illumination widthwise of the web, or even a wide tungsten source such as a rectilinear filament lamp may be used. Where a wide web is concerned, the average cross measurement may be had or if desired in addition or alternatively a measure of the variation in web cross measurement across the width of the web.

The transmission of infra-red through a thick textile structure is found to be non-linear. Whereas with a thin fleece with less than about 75% obscuration, the transmission of visible light is approximately linear with web density (say in terms of weight per unit area), with thick fleeces where transmission is predominantly through rather than between fibres, the transmitted energy falls off more rapidly with increasing obscuration and the rate of fall off appears in many instances to be approximately exponential. So as to present a meaningful indication of a cross measurement, the signal from an infra-red sensor in a measuring arrangement according to the invention can be linearised electronically, for example, digitally.

The method can be adapted for measuring the thickness of a thick fibre web, even to such a thickness as may be appropriate for a carpet backing or facing, say from 50 to as much as 1,000 grams per square meter. The thickness can be determined from the transmission measurement assuming a known volume density. On the other hand, if the thickness is known, volume density can be measured. The measurement is, however, found to approximate to area density, which is of most importance in a textile context.

Other variables can also be measured, for example the extent of bonding in an adhesively bonded fibre web or the thickness or regularity of an adhesive or backing layer, or the degree of thermobonding of a thermobonded web, it being merely necessary that sufficient infra-red radiation is transmitted to be detectable.

The invention also comprises apparatus for measuring across a thick textile structure comprising an infra-red source disposed on one side of support means for said structure and detector means disposed on the other side of said support means, and indicating means indicating the measurement.

The indicating means may comprise an analogue or a digital indicator calibrated to a selected variable such as web density in terms of weight per unit area.

BRIEF DESCRIPTION OF THE DRAWINGS

One embodiment of apparatus and a method for measuring across a thick textile structure will now be described with reference to the accompanying drawing in which.

DETAILED DESCRIPTION OF THE PREFERRED EMBODIMENTS

Figure 1:
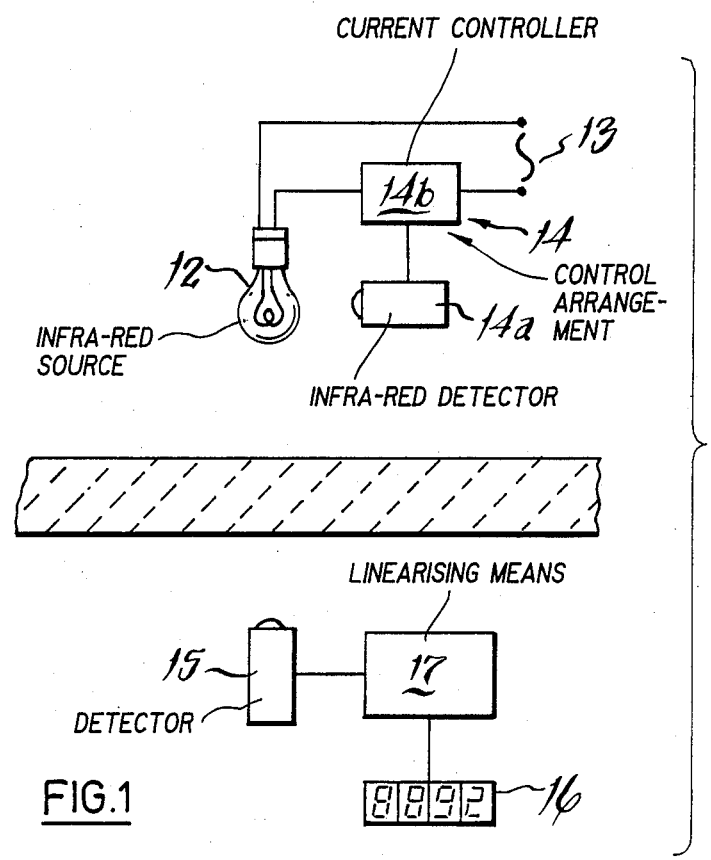
FIG. 1 is a diagrammatic representation.

The Figure illustrates a method and apparatus for measuring across a thick textile structure 11, which may comprise a thick fleece having a weight per unit area of from, say, 50 to 1,000 grams per square meter, or a thermobonded fleece or an adhesively bonded fleece or an adhesively bonded laminated structure or a foam backed structure or the like of which it is desired to measure the thickness or the volume density or the area density or other property.

An infra-red source 12 comprises a tungsten lamp run at a dull glow from a mains supply 13 controlled by a control arrangement 14.

The control arrangement 14 comprises a photocell or infra-red detector 14a which monitors the output of the lamp 12 and which is connected to a current controller 14b in such manner as to maintain the lamp output at a desired constant value.

Infra-red radiation transmitted through the structure 11 is detected at a detector 15 which can be of the type used, for example, in heat-seeking missiles or such other available detector as may be appropriate.

The detector 15 is connected to indicating means 16 suitably calibrated to indicate the desired variable. Since the fall off of transmitted infra-red radiation will often be exponential with increasing web density, it will be desirable to linearise the output of the detector 15 in linearising means 17, which may comprise comparator means comparing the input signal from the detector 15 with a set of standard signals, perhaps as many as fifty in number and assigning an output to the indicating means according to which standard signal the detector 15 input signal compares to. The output may bear a logarithmic relation to the input, so as to compensate for the exponential of the transmission strength to the quantity being measured.

Although the detectors 15 may be expected to be reasonably similar in their characteristics, they may nevertheless display some differences which can, however, be compensated for by calibration. The calibration can involve illuminating the detectors 15 with no fleece present at two different irradiation levels and noting the output voltages of the detectors. The reading from each photodiode can be subsequently adjusted (as in a programmed microprocessor) by a correction factor (assuming the response of each detector 15 to be suitably linear over the illumination range).

The apparatus may be situated at any convenient place in a fleece path, especially just before or just after a point at which web density may be controlled or at which a faulty web needs to be detected.

An alternative method of using the apparatus would be to adjust the lamp current until a predetermined signal is obtained from the detector 15 and note the value of current required as an indication of the web density.

It may be necessary to control the surrounding conditions as by shielding against draughts and strong light from the sun, lighting and machinery in order to avoid spurious readings.

Even in a relatively unsophisticated form, the arrangement has been found capable of readily detecting a change in the area density of a thick cross-folded card web at a cross-folding fault where an over plate is followed by an under plate.

It would be possible to use the apparatus in an inspecting operation for finished fabric, where it might be combined with an optical inspection arrangement using visible light detecting a wider range of fabric faults than either visible light or infra-red used alone.

Figure 2:
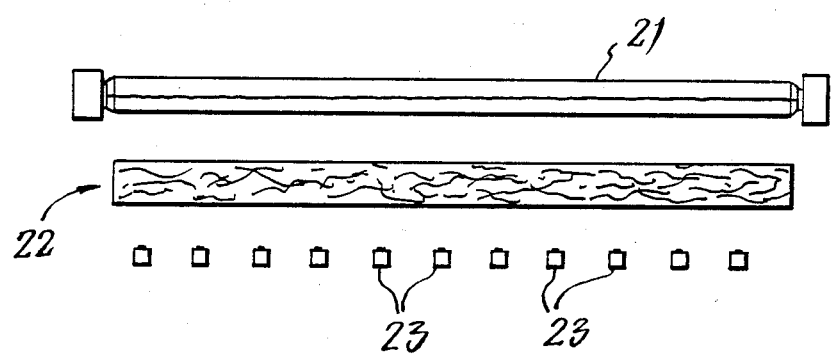
FIG. 2 is a diagrammatic elevation of a wide fleece measuring arrangement.
Figure 3:
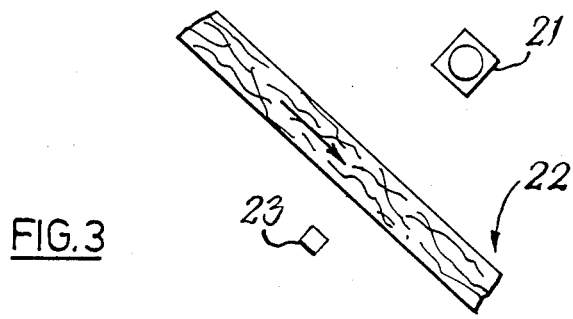
FIG. 3 is a side view of the arrangement of FIG. 2.

For wide webs, of course, as indicated above, multiple discrete infra-red sources would be used or a single elongate infra-red filament lamp giving a uniform or substantially uniform illumination over the width of the web, and multiple infra-red detectors would be disposed on the opposite side of the web, which could be averaged or which could be indicated seperately so as to give either an average web density or other cross measurement or a distribution of, for instance, web area density, over the width of the web. FIGS. 2 and 3 illustrate an arrangement for wide webs including a web-wide elongate filament lamp 21 situated above an inclined web path 22 opposite a battery of infra-red detectors 23. Situating the lamp 21 above the web exposes the web to infra-red radiation, but not to convected heat, and so is less deleterious to sensitive webs (e.g. of wool) than if the source were beneath the web. The inclined web path means that dust and fly has reduced tendency to settle on the detectors 23.

Figure 4:
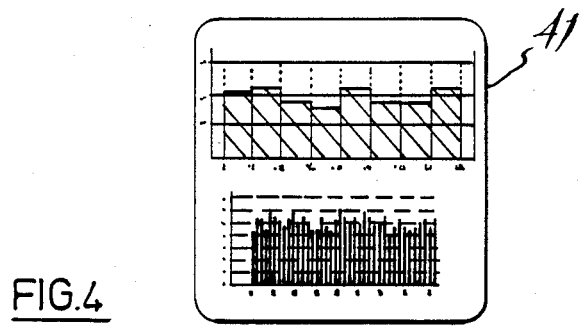
FIG. 4 is a view of a display screen indicating the results of measurement.

FIG. 4 illustrates indicating means 41 for indicating the lengthwise and transverse distribution of measurements of a travelling web. The display comprises a video screen or visual display unit (VDU) with a split screen arrangement of which the upper half comprises a bar chart showing the measurement from each of the IR detectors of the embodiment of FIGS. 2 and 3 for example, while the lower half comprises a bar chart, updated every minute, of the average of the detectors' measurements. Between them, these two indications serve as an indication of the uniformity, transverse and lengthwise, of the web. Instead of a video screen, a liquid cyrstal or other display type can be used.

What we claim:

1. A method for measuring area density of a fibrous web, of the type used in the production of yarns and non-woven fabrics, the web being of such area density that its fibres obsure at least 75% of light transmitted across the web, comprising illuminating the web from one side with radiation from an infrared source and detecting the transmitting infra-red radiation on the other side of the web by a plurality of detectors spaced apart over the width of the web wherein said detectors output signals representative of an approximately exponential function of area denisty, and linearising and calibrating said signals to give signals representative of area density.

2. A method according to claim 1, in which said infra-red source comprises a wide-band source.

3. A method according to claim 1, in which said infra-red source comprises a tungsten lamp run at a dull glow.

4. A method according to claim 1, in which the linearisation is effected digitally.

5. A method according to claim 1, wherein the web is a moving textile structure, and the textile structure is contiuously measured.

6. Apparatus for measuring area density of a fibrous web, of the type used in the production of yarns and non-woven fabrics and is of such area density that its fibres obscure at least 75% of light transmitted across the web, comprising an infra-red source, web support means for said web, said infra-red source being disposed on one side of said web support means, infra-red detection means disposed on the other side of said support means to said source and comprising a plurality of detectors spaced apart over the width of the web and illuminated by infra-red radiatron transmitted through the web when supported by said support means so as to give output signals representative of an approximately exponential function of web area density, and linearising means linearising the output of said detection means to give signals representative of area density.

7. Apparatus according to claim 6, said infra-red source comprising a wide-band source.

8. Apparatus according to claim 6, said infra-red source comprising a tungsten lamp and comprising electric supply means therefor adapted to run said tungsten lamp at a dull glow.

9. Apparatus according to claim 6, said linearising means comprising digital linearising means.

* * * * *